(12) United States Patent
Goto et al.

(10) Patent No.: US 11,623,198 B2
(45) Date of Patent: Apr. 11, 2023

(54) ULTRASOUND GENERATION MEMBER, ULTRASOUND EMISSION DEVICE, AND ULTRASOUND DENATURATION OBSERVATION DEVICE

(71) Applicants: OSAKA UNIVERSITY, Osaka (JP); CORONA ELECTRIC Co., Ltd., Ibaraki (JP)

(72) Inventors: Yuji Goto, Suita (JP); Hirotsugu Ogi, Suita (JP); Masatomo So, Suita (JP); Kensuke Ikenaka, Suita (JP); Hideki Mochizuki, Suita (JP); Shinichi Hashimoto, Hitachinaka (JP)

(73) Assignees: OSAKA UNIVERSITY, Osaka (JP); CORONA ELECTRIC Co., Ltd., Ibaraki (JP)

( * ) Notice: Subject to any disclaimer, the term of this patent is extended or adjusted under 35 U.S.C. 154(b) by 543 days.

(21) Appl. No.: 16/627,086

(22) PCT Filed: Apr. 19, 2018

(86) PCT No.: PCT/JP2018/016164
§ 371 (c)(1),
(2) Date: Dec. 27, 2019

(87) PCT Pub. No.: WO2019/003601
PCT Pub. Date: Jan. 3, 2019

(65) Prior Publication Data
US 2020/0139337 A1    May 7, 2020

(30) Foreign Application Priority Data

Jun. 29, 2017    (JP) .............................. JP2017-127224

(51) Int. Cl.
*B01J 19/10* (2006.01)
*G01N 1/38* (2006.01)
(Continued)

(52) U.S. Cl.
CPC ................. *B01J 19/10* (2013.01); *B06B 1/02* (2013.01); *G01N 1/38* (2013.01); *H01L 41/00* (2013.01)

(58) Field of Classification Search
CPC ........... B01J 19/10; G01N 1/38; G01N 33/49; G01N 2021/1789; G01N 21/1717;
(Continued)

(56) References Cited

U.S. PATENT DOCUMENTS

2005/0031499 A1    2/2005  Meier
2007/0238090 A1   10/2007  Hukari et al.

FOREIGN PATENT DOCUMENTS

JP    2004-361251 A    12/2004
JP    2005-094552 A     4/2005
(Continued)

OTHER PUBLICATIONS

International Search Report; issued in PCT/JP2018/016164; dated Jun. 19, 2018.

*Primary Examiner* — Daniel L Murphy
(74) *Attorney, Agent, or Firm* — Studebaker & Brackett PC

(57) ABSTRACT

An ultrasound generation member according to an aspect of the present invention includes an ultrasound generation element configured to emit ultrasound in a direction of a target object in one specific container of a plurality of containers. An ultrasound emission device according to an aspect of the present invention includes the ultrasound generation member, and a drive power supply configured to apply voltage across the ultrasound generation element of the ultrasound generation member. An ultrasound emission device according to an aspect of the present invention includes the ultrasound generation member that includes, as the ultrasound generation element, a plurality of ultrasound generation elements, and a drive power supply configured to
(Continued)

apply voltage across the plurality of ultrasound generation elements of the ultrasound generation member.

11 Claims, 16 Drawing Sheets

(51) Int. Cl.
*H01L 41/00* (2013.01)
*B06B 1/02* (2006.01)

(58) Field of Classification Search
CPC ............. G01N 21/6486; G01N 35/028; G01N 2035/00554; G01N 1/28; H01L 41/00; B06B 1/02; B06F 31/85; B06F 33/813; H04R 17/00
USPC .......................................................... 310/311
See application file for complete search history.

(56) References Cited

FOREIGN PATENT DOCUMENTS

| | | |
|---|---|---|
| JP | 2005-211837 A | 8/2005 |
| JP | 2009-068921 A | 4/2009 |
| WO | 2012/017739 A1 | 2/2012 |

ULTRASOUND GENERATION MEMBER, ULTRASOUND EMISSION DEVICE, AND ULTRASOUND DENATURATION OBSERVATION DEVICE

TECHNICAL FIELD

The present invention relates to an ultrasound generation member, an ultrasound emission device, and an ultrasound denaturation observation device.

BACKGROUND ART

Ultrasound is used in a variety of applications. For example, ultrasound is used for fragmenting cells, suspending mixture, micronizing solids, dissolving solids, and accelerating reactions. It is also known that ultrasound is utilized for accelerating formation of amyloid fibrils, and dividing and refining the amyloid fibrils.

For example, an ultrasonic generator in which ultrasonic vibrators are provided outside a treatment tank is described in Patent Literature 1. The ultrasonic generator of Patent Literature 1 automatically controls ultrasound emission and interruption thereof in a state where a holder to which sealed tubes are fixed is disposed in an upper part of the treatment tank with respective tips of the sealed tubes immersed in water in the treatment tank. The ultrasonic generator of Patent Literature 1 is provided with a timer that controls ultrasound oscillation and a counter that counts the number of times the timer is activated, thereby enabling repetition of the ultrasound emission at predetermined intervals.

CITATION LIST

Patent Literature

[Patent Literature 1]
JP 2005-211837A

SUMMARY OF INVENTION

Technical Problem

In the ultrasonic generator of Patent Literature 1, ultrasound generated by each ultrasonic vibrator is emitted to the entire sealed tubes through the water in the treatment tank. The configuration causes intensity dispersion of ultrasound to be transmitted to the sealed tubes depending on the position of the sealed tubes in the holder. The ultrasonic generator of Patent Literature 1 also enables the ultrasonic vibrators to emit ultrasound to the sealed tubes at once, but it is impossible to adjust ultrasound intensity and ultrasound emission timing for each of the sealed tubes.

The present invention has been achieved in view of the above circumstances, and a target object thereof is to provide an ultrasound generation member, an ultrasound emission device, and an ultrasound denaturation observation device, capable of emitting ultrasound controlled according to a specific container that contains a target object.

Solution to Problem

An ultrasound generation member according to an aspect of the present invention includes an ultrasound generation element that emits ultrasound to a target object in one specific container of a plurality of containers.

In an embodiment, the ultrasound generation element includes an oscillator, a first electrode provided for the oscillator, and a second electrode provided for the oscillator.

In an embodiment, the oscillator is elongated in a longitudinal direction, and the first and second electrodes are elongated in a direction that is the same as the longitudinal direction in which the oscillator is elongated.

In an embodiment, the ultrasound generation element further includes an acoustic coupling member connected to the oscillator.

In an embodiment, the ultrasound generation member includes, as the ultrasound generation element, a plurality of ultrasound generation elements.

In an embodiment, the ultrasound generation member further includes a holding member that holds the plurality of ultrasound generation elements.

An ultrasound emission device according to an aspect of the present invention includes an ultrasound generation member described above, and a drive power supply that applies voltage across the ultrasound generation element of the ultrasound generation member.

An ultrasound emission device according to an aspect of the present invention includes an ultrasound generation member described above, and a drive power supply that applies voltage across the plurality of ultrasound generation elements of the ultrasound generation member.

In an embodiment, the drive power supply applies the voltage across the plurality of ultrasound generation elements so that the plurality of ultrasound generation elements sequentially emits ultrasound.

An ultrasound denaturation observation device according to an aspect of the present invention includes an ultrasound emission device described above, and an observation section that observes a denaturation of the target object.

Advantageous Effects of Invention

The present invention enables emission of ultrasound controlled according to the specific container that contains the target object.

DESCRIPTION OF EMBODIMENTS

An ultrasound generation member, an ultrasound emission device, and an ultrasound denaturation observation device according to embodiments of the present invention will hereinafter be described with reference to accompanying drawings. The present invention is however not limited to the embodiments below.

Figure 1A:
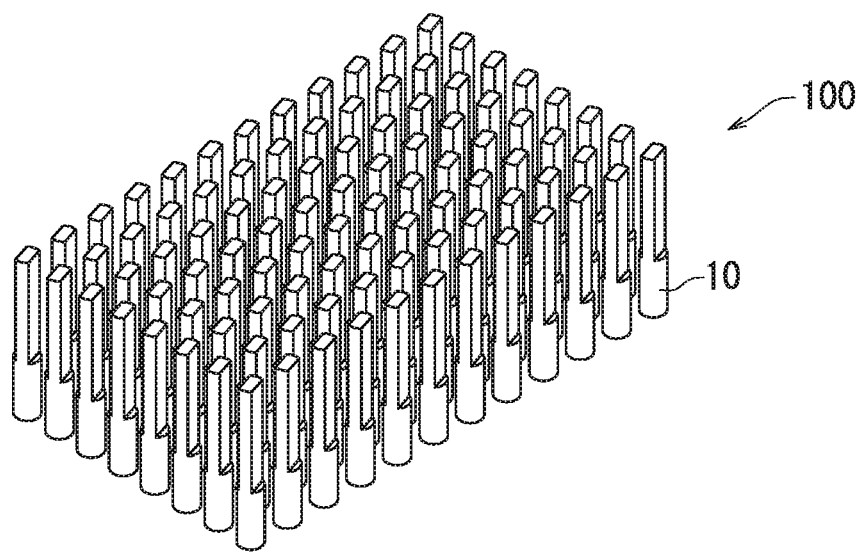
FIG. 1A is a schematic illustration depicting an ultrasound generation member according to an embodiment of the present invention.

An ultrasound generation member 100 according to an embodiment of the present invention will first be described with reference with FIGS. 1A and 1B. FIG. 1A is a schematic illustration depicting the ultrasound generation member 100.

The ultrasound generation member 100 includes ultrasound generation elements 10. The ultrasound generation elements 10 are arranged in a matrix with a predetermined number of rows and a predetermined number of columns. When voltage is applied across the ultrasound generation elements 10, each of the ultrasound generation elements 10 generates ultrasound. Each of the ultrasound generation elements 10 generates ultrasound whose intensity and frequency are controllable for each of the ultrasound generation elements 10. The ultrasound generation member 100 is mounted on for example a microplate.

Figure 1B:
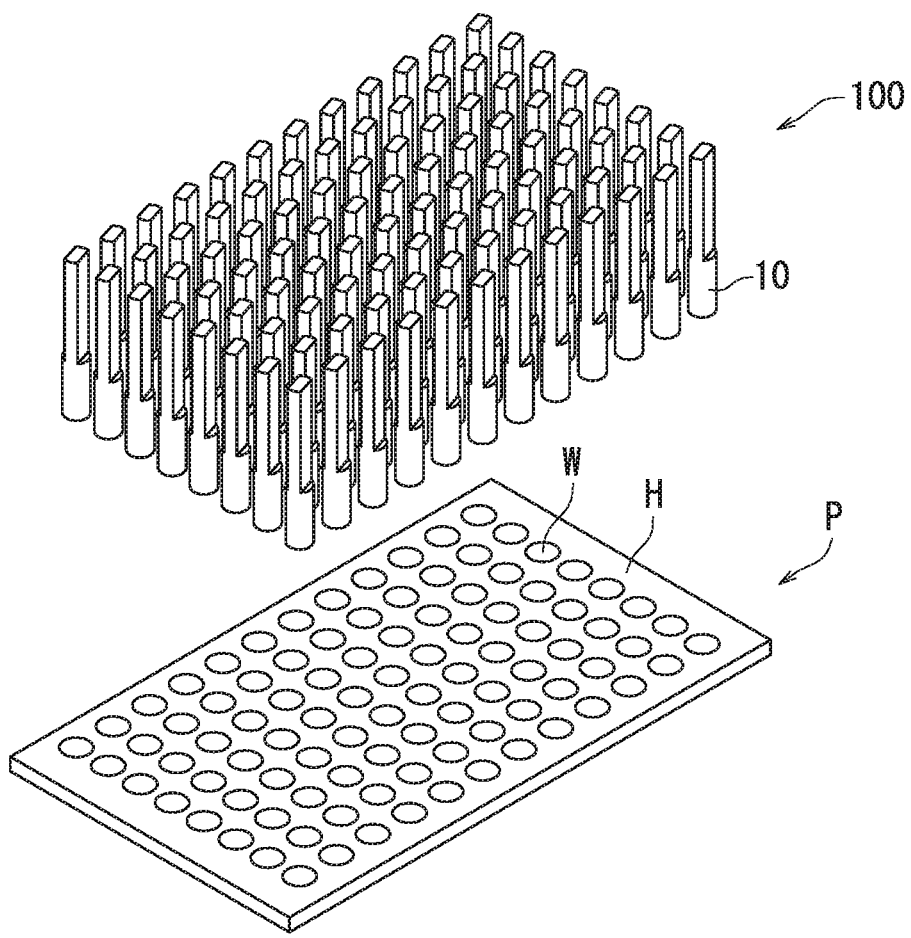
FIG. 1B is a schematic illustration depicting the ultrasound generation member, before being mounted on a microplate, according to the present embodiment.

FIG. 1B is a schematic illustration depicting the ultrasound generation member 100 before being mounted on the microplate P. The microplate P has a flat section H and wells W recessed in the flat section H. Each well W is defined so as to be surrounded by a bottom wall and a side wall.

The wells W are separated from each other, and each of the wells functions as an individual container. For example, each well W has an opening that is greater than or equal to 1 mm and less than or equal to 10 mm in diameter. Each well W is also greater than or equal to 1 mm and less than or equal to 30 mm in depth.

The wells W are formed in the microplate P and arranged in the matrix with the predetermined number of rows and the predetermined number of columns. For example, the wells are 96 in number and arranged in a matrix with 12 rows and 8 columns.

In the ultrasound generation member 100 according to the present embodiment, each ultrasound generation element 10 is disposed at a specific well W (container) of the containers. For example, the ultrasound generation element 10 in a first row and a first column is disposed at a corresponding well W in a first row and a first column, and the ultrasound generation element 10 in a second row and a first column is disposed at a corresponding well W in a second row and a first column.

In the ultrasound generation member 100 according to the present embodiment, an aperture area of each of the wells W in the microplate P has size corresponding to a sectional area of each of the ultrasound generation elements 10. Here, respective aperture areas of the wells W in the microplate P are slightly larger than respective sectional areas of the ultrasound generation elements 10. This allows the ultrasound generation elements 10 of the ultrasound generation member 100 to be individually inserted into the wells W of the microplate P.

Here, the number of the wells W in the microplate P is equal to the number of the ultrasound generation elements 10 of the ultrasound generation member 100. Into each well W, one corresponding ultrasound generation element 10 is inserted.

Typically, target objects are individually added to the wells W of the microplate P, and then the ultrasound generation elements 10 are individually inserted into the wells W. When voltage is applied across the ultrasound generation elements 10, each of the ultrasound generation elements 10 emits ultrasound to the target object in a corresponding well W. Each of the ultrasound generation elements 10 emits ultrasound to the target object in a corresponding well W, thereby enabling the ultrasound generation member 100 to individually emit ultrasound controlled for each of the target objects in the wells W with respect to the target objects.

Note that each target object may be a liquid. The liquid is typically a solution. Alternatively, each target object may be gel or powder.

For example, when the target object in each well W is a supersaturated solution, the ultrasound generation member 100 individually emitting ultrasound to the supersaturated solutions in the wells W enables precipitation of solutes dissolved in the supersaturated solutions.

Figure 2A:
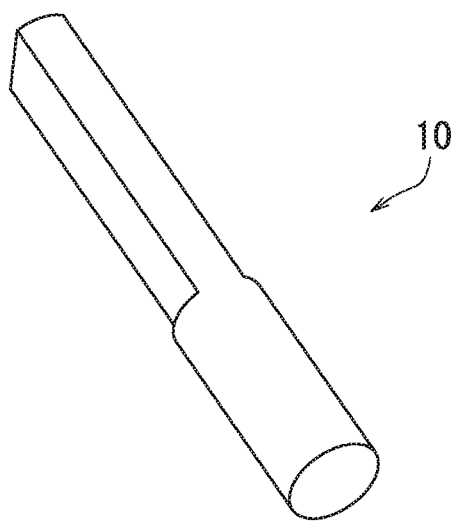
FIG. 2A is a perspective view of one ultrasound generation element in the ultrasound generation member according to the present embodiment.
Figure 2B:
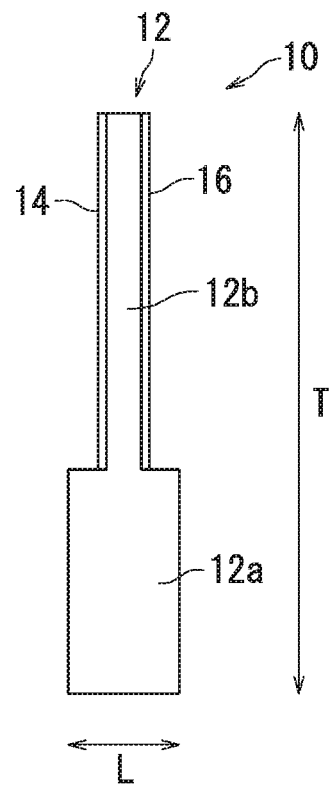
FIG. 2B is a side view of the ultrasound generation element.

The ultrasound generation elements 10 of the ultrasound generation member 100 will next be described with reference to FIGS. 2A and 2B. FIG. 2A is a schematically perspective view of one ultrasound generation element 10, and FIG. 2B is a schematically cross-sectional view of the one ultrasound generation element 10.

The ultrasound generation element 10 has a rod shape and is elongated in a longitudinal direction thereof. The ultrasound generation element 10 has width L and height T that is larger than the width L. It is preferable that the height T of the ultrasound generation element 10 have size that is 3 through 20 times larger than the width L of the ultrasound generation element 10. For example, the ultrasound generation element 10 is greater than or equal to 30 mm and less than or equal to 100 mm in height T, and greater than or equal to 3 mm and less than or equal to 6 mm in width L.

The width (diameter) L of the ultrasound generation element 10 is also smaller than a diameter of each well W of the microplate P illustrated in FIG. 1B. This allows at least a part of the ultrasound generation element 10 to be inserted into each well W of the microplate P.

It is preferable that the height T of the ultrasound generation element 10 be larger than depth of each well W of the microplate P illustrated in FIG. 1B. In this case, a remaining part of the ultrasound generation element 10 protrudes from the flat section H of the microplate P even with the ultrasound generation element 10 inserted into a well W of the microplate P up to the bottom of the well W. This enables easy connection between the ultrasound generation element 10 and an unillustrated external power supply without immersing the remaining part of the ultrasound generation element 10 in the target object in the well W.

As illustrated in FIG. 2B, the ultrasound generation element 10 includes an oscillator 12, an electrode 14, and an electrode 16. The oscillator 12 is elongated in the longitudinal direction. Typically, the oscillator 12 is disposed with the longitudinal direction of the oscillator 12 being parallel to a vertical direction.

Here, the oscillator 12 is made of a material having a piezoelectric effect. For example, the oscillator 12 contains lead zirconate titanate (PZT). Alternatively, the oscillator 12 may contain polyvinylidene fluoride (PVDF), crystal, langasite ($La_3Ga_5SiO_{14}$), barium titanate, or lead titanate. Alternatively, the oscillator 12 may be made of magnetic material exhibiting magnetostriction. In this case, in place of the electrodes 14 and 16, the ultrasound generation element 10 includes an element that generates an oscillating magnetic field around the oscillator 12. For example, the ultrasound generation element 10 includes a solenoidal coil surrounding a periphery of the oscillator 12, thereby enabling application of the oscillating magnetic field in the longitudinal direction of the oscillator 12.

Here, the oscillator 12 has a shape in which, of a cylindrical piezoelectric material, two opposite places are cut parallel to a center axis of the cylindrical piezoelectric material. Both ends of the oscillator 12 are therefore flat. One end of the ends of the oscillator 12 is circular in plan view as seen from the one end of the oscillator 12. A different end of the ends of the oscillator 12 has a shape in which two arcs are connected by two straight lines in plan view from the different end of the oscillator 12.

The oscillator 12 has a portion 12a and a portion 12b. Here, the portion 12a has a cylindrical shape, and the portion 12b has a shape in which of a peripheral surface of the cylindrical shape, faces that are opposite each other are cut. Note that the portion 12b may be a cuboid.

The electrodes 14 and 16 are provided so as to be elongated in a direction that is the same as the longitudinal direction of the oscillator 12. The electrode 14 is provided at one of the cut parts of the portion 12b, while the electrode 16 is provided at the other of the cut parts of the portion 12b.

Note that the electrodes 14 and 16 are provided at the portion 12b and not provided at the portion 12a. Each of the electrodes 14 and 16 contains for example platinum.

The portion 12b sandwiched between the electrodes 14 and 16 has a relatively narrow width. Thus, the ultrasound generation element 10 according to the present embodiment has a transverse polarization structure. It is therefore possible to generate a high electric field around the portion 12 and generate ultrasound having prescribed frequency and a relatively strong intensity even if a relatively low voltage is applied between the electrodes 14 and 16. Note that although an outer periphery of the portion 12b provided with the electrodes 14 and 16 is shorter than an outer periphery of the portion 12a without the electrodes 14 and 16 in this example, the outer periphery of the portion 12b provided with the electrodes 14 and 16 may be longer than the outer periphery of the portion 12a without the electrodes 14 and 16.

Note that the ultrasound generation element 10 vibrates according to the frequency of the voltage applied thereacross. It is preferable that the ultrasonic generator element 10 be of suitable size for resonance which occurs at the frequency of the ultrasound emitted therefrom. For example, when the ultrasound generation element 10 emits ultrasound at a frequency of 30 kHz, the ultrasound generation element 10 is preferably greater than or equal to 4 mm and less than or equal to 5 mm in width L, and greater than or equal to 50 mm and less than or equal to 60 mm in height T.

Figure 3:
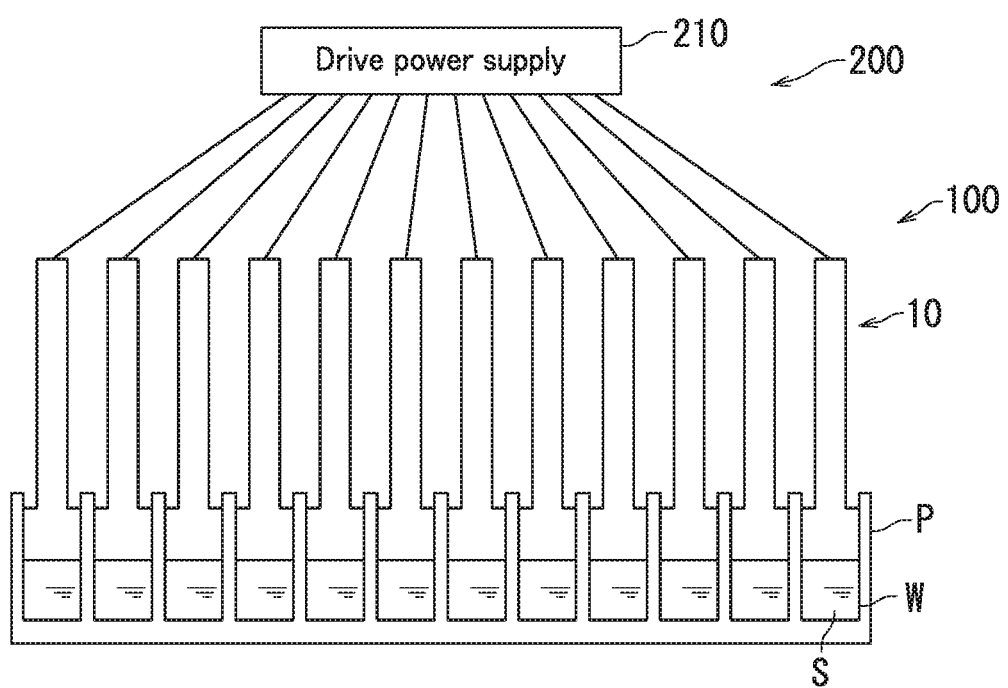
FIG. 3 is a schematic illustration depicting an ultrasound emission device according to an embodiment of the present invention.

An ultrasound emission device 200 according to an embodiment of the present invention will next be described with reference with FIG. 3. FIG. 3 is a schematic illustration depicting the ultrasound emission device 200 according to the present embodiment.

The ultrasound emission device 200 includes an ultrasound generation member 100 and a drive power supply 210. The drive power supply 210 applies voltage across ultrasound generation elements 10 of the ultrasound generation member 100.

Wells W of a microplate P individually contain target objects S. The ultrasound generation member 100 is mounted on the microplate P. When the drive power supply 210 applies voltage across the ultrasound generation elements 10 of the ultrasound generation member 100, ultrasound generated from each ultrasound generation element 10 is propagated to the target object S in a corresponding well W. When the ultrasound is propagated to the target object S, a change occurs in the target object S. Here, examples of the change include pulverization, suspending, micronization, dissolution, stir, heating, agglomeration, and reaction acceleration. For example, when the target object S is a supersaturated solution of amyloid, the ultrasound is propagated to the target object S and then a supersaturated solute aggregates and precipitates amyloid.

In the ultrasound emission device 200 according to the present embodiment, the one ultrasound generation element 10 emits ultrasound to the target object S in the one specific well (container) of the containers. For example, the ultrasound generation element 10 in a first row and a first column emits ultrasound to the target object S in the well W in a first row and a first column, and the ultrasound generation element 10 in a second row and a first column emits ultrasound to the target object S in the well W in a second row and a first column. Different ultrasound generation elements 10 enable individual ultrasound of different intensity and different frequency. It is therefore possible to emit ultrasound controlled according to the specific well (container) that contains the target object.

Note that here, the ultrasound generation elements 10 of the ultrasound generation member 100 are individually inserted into the wells W that individually contain the target objects S. Each ultrasound generation element 10 is accordingly in contact with a corresponding target object S. and is to emit ultrasound to the corresponding target object S in that state. The ultrasound generation elements 10 need not necessarily be individually inserted into the wells W as long as each ultrasound generation element 10 can emit ultrasound to the target object S in a corresponding well W.

For example, the drive power supply 210 may apply voltage across each of the ultrasound generation elements 10 at the same time so that the ultrasound generation elements 10 individually emit ultrasound at the same timing. Alternatively, the drive power supply 210 may apply voltage across each of the ultrasound generation elements 10 at different timing so that the ultrasound generation elements 10 individually emit ultrasound at different timing. For example, the drive power supply 210 may sequentially apply voltage across each of the ultrasound generation elements 10.

The drive power supply 210 may also apply voltage (of identical frequency, identical voltage level, and identical emission time of ultrasound) across each of the ultrasound generation elements 10 so that each of the ultrasound generation element 10 emits ultrasound (of identical frequency, identical intensity, and identical emission time) to a corresponding target object S in the different wells W of the microplate P. Alternatively, drive power supply 210 may apply voltage (of different frequency, different voltage level, and/or different emission time of ultrasound) across each of the ultrasound generation elements 10 so that each of the ultrasound generation element 10 emits ultrasound (of different frequency, different intensity, and/or different emission time) to a corresponding target object S in the different wells W of the microplate P.

Note that identical type of target objects S are preferably contained in the wells W of the microplate P. The target objects S may however be the same as or different from each other. For example, when the target objects S are the same as each other, solution components and solution concentrations between the target objects are the same as each other. In contrast, when the target objects S are different from each other, at least one of the solution components and the solution concentrations between the target objects typically differ from the other.

For example, reaction products generated under the same reaction conditions become identical target objects, and reaction products generated under partially different reaction conditions become different target objects. Alternatively, samples (for example blood and the like) collected at once from the same subject are identical target objects, and samples collected from different subjects are different target objects. Samples (blood, etc.) collected from the same subject at different timings are also different target objects.

When each of the ultrasound generation elements 10 emits ultrasound (of different frequency, different intensity, and different emission time) to an identical target objects contained in a corresponding well W of the microplate P, a change according to the frequency, intensity, and emission time of the ultrasound in the identical target objects can be measured at once. Alternatively, when the ultrasound generation elements 10 individually emit ultrasound (of identical frequency, identical intensity, and identical emission time) to different target objects contained in the wells W of the microplate P, respective changes due to the ultrasound in the different target objects can be measured at once.

Note that the target objects contained in the wells W of the microplate P may be different types of target objects and not limited to the identical type of target objects.

As stated above, the drive power supply 210 may sequentially apply voltage across each of the ultrasound generation elements 10.

Figure 4A:
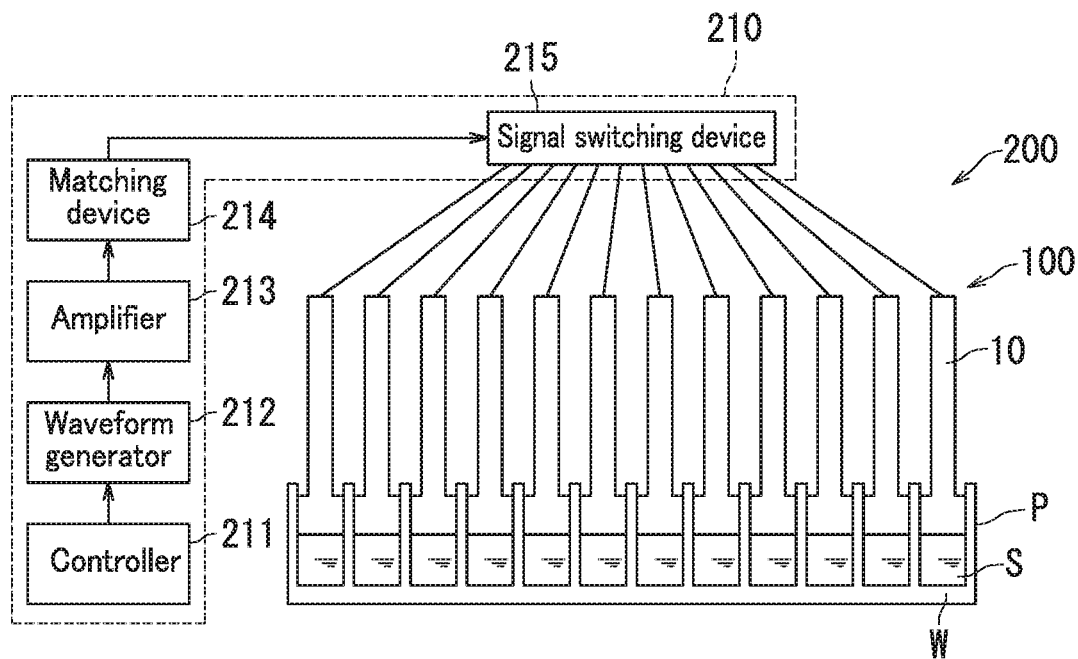
FIG. 4A is a schematic illustration depicting an ultrasound emission device according to an embodiment.

An ultrasound emission device 200 according to an embodiment of the present invention will next be described with reference to FIGS. 4A and 4B. FIG. 4A is a schematic illustration depicting the ultrasound emission device 200 according to the present embodiment.

The ultrasound emission device 200 includes an ultrasound generation member 100 and a drive power supply 210. The ultrasound generation member 100 includes ultrasound generation elements 10.

The drive power supply 210 includes a controller 211, a waveform generator 212, an amplifier 213, a matching device 214, and a signal switching device 215. The controller 211 designates waveform of a signal to be output from the waveform generator 212. The controller 211 is for example a personal computer. The waveform generator 212 outputs the signal whose waveform is designated by the controller 211. The amplifier 213 amplifies the signal that is output from the waveform generator 212. Impedance is matched by the matching device 214 with respect to the signal that is output from the amplifier 213. Accordingly, voltage having predetermined amplitude and predetermined frequency is generated.

The signal switching device 215 switches to an ultrasound generation element 10 to which the voltage is applied. Here, the ultrasound generation member 100 includes 96 ultrasound generation elements 10, and the signal switching device 215 switches between respective electrical connection with the ultrasound generation elements 10 so that the voltage is sequentially applied across the 96 ultrasound generation elements 10.

The signal switching device 215 switches, at predetermined intervals, to an ultrasound generation element 10 to which the voltage is to be applied. For example, the signal switching device 215 switches, every 0.3 seconds, to an ultrasound generation element 10 to which the voltage is to be applied.

Figure 4B:
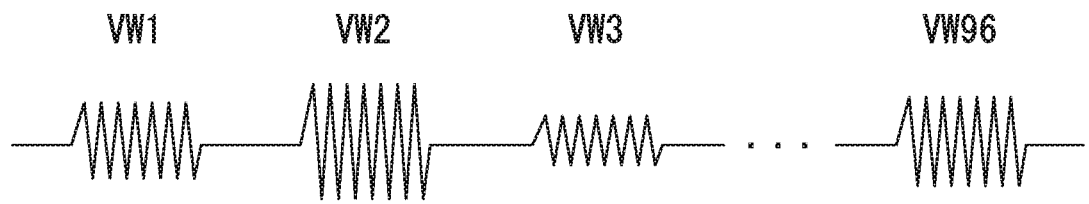
FIG. 4B is a schematic illustration depicting a waveform of voltage applied across each of different ultrasound generation elements.

FIG. 4B is a schematic illustration depicting a waveform of voltage applied across each of the ultrasound generation elements 10.

The waveform generator 212 sequentially outputs a waveform signal VW1, a waveform signal VW2, a waveform signal VW3, . . . , and a waveform signal VW96 according to instructions from the controller 211. The amplifier 213 amplifies voltage that is sequentially output from the waveform generator 212.

The signal switching device 215 performs switching so that voltage is sequentially applied across the ultrasound generation elements 10. For example, the signal switching device 215 is first electrically connected with a first ultrasound generation element 10, and the voltage of the waveform signal VW1 is applied across the first ultrasound generation element 10. The signal switching device 215 is subsequently electrically disconnected from the first ultrasound generation element 10, and electrically connected with a second ultrasound generation element 10. The voltage of the waveform signal VW2 is consequently applied across the second ultrasound generation element 10. The signal switching device 215 is subsequently electrically disconnected from the second ultrasound generation element 10, and electrically connected with a third ultrasound generation element 10. The voltage of the waveform signal VW3 is consequently applied across the third ultrasound generation element 10. Subsequently, electrical disconnection from a connected ultrasound generation element 10, and electrical connection with and voltage application to a next ultrasound generation element 10 are similarly repeated.

The voltage of the waveform signal VW96 is applied across the last ultrasound generation element 10, and then the electrical connection with the last ultrasound generation element 10 is disconnected. The electrical connection of the first ultrasound generation element 10 is then established, and the voltage of the waveform signal VW1 is applied across the first ultrasound generation element 10 again. Thereafter, the application of voltage of a specific waveform to each ultrasound generation element 10 is similarly repeated a predetermined number of times or for a predetermined time.

The ultrasound emission device 200 described above with reference to FIGS. 4A and 4B supplies the ultrasound generation elements 10 with voltage at different timing, thereby enabling manufacture of drive power supplies 210 with a relatively simple configuration and emission of ultrasound controlled for each of the ultrasound generation elements 10.

Note that preferably the ultrasound generation elements 10 are held by the ultrasound generation member 100 with a predetermined positional relationship maintained.

Figure 5A:
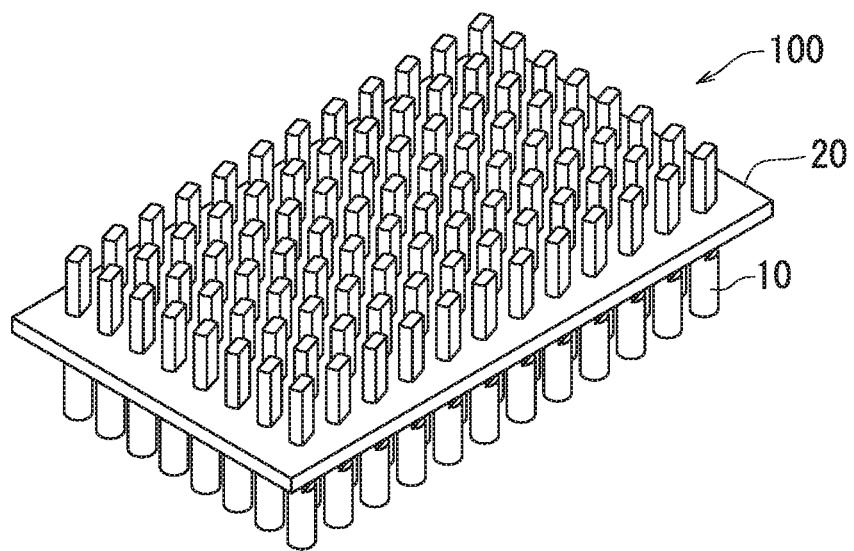
FIG. 5A is a schematic illustration depicting an ultrasound generation member according to an embodiment of the present invention.

An ultrasound generation member 100 according to an embodiment of the present invention will next be described with reference with FIGS. 5A and 5B. FIG. 5A is a schematic illustration depicting the ultrasound generation member 100 according to the present embodiment.

The ultrasound generation member 100 includes ultrasound generation elements 10, and a holding member 20 that holds the ultrasound generation elements 10. The holding member 20 is provided with holes individually corresponding to the ultrasound generation elements 10. Here, the holes are provided in the holding member 20 in a matrix with 12 rows and 8 columns.

The ultrasound generation elements 10 are individually inserted into the holes of the holding member 20. The holding member 20 holds the ultrasound generation elements 10 with the ultrasound generation elements 10 individually inserted into the holes of the holding member 20. Respective one ends of the ultrasound generation elements 10 in a longitudinal direction thereof protrude from one surface of the holding member 20, while respective other ends of the ultrasound generation elements 10 in the longitudinal direction protrude from another surface of the holding member 20.

The ultrasound generation member 100 according to the present embodiment causes the holding member 20 to hold the ultrasound generation elements 10, thereby allowing the ultrasound generation elements 10 to be moved together with a positional relationship among the ultrasound generation elements 10 maintained. Note that the holding member 20 preferably holds the ultrasound generation elements 10 so as to be in contact with vibration nodes of oscillators 12 that vibrate during voltage application.

Figure 5B:
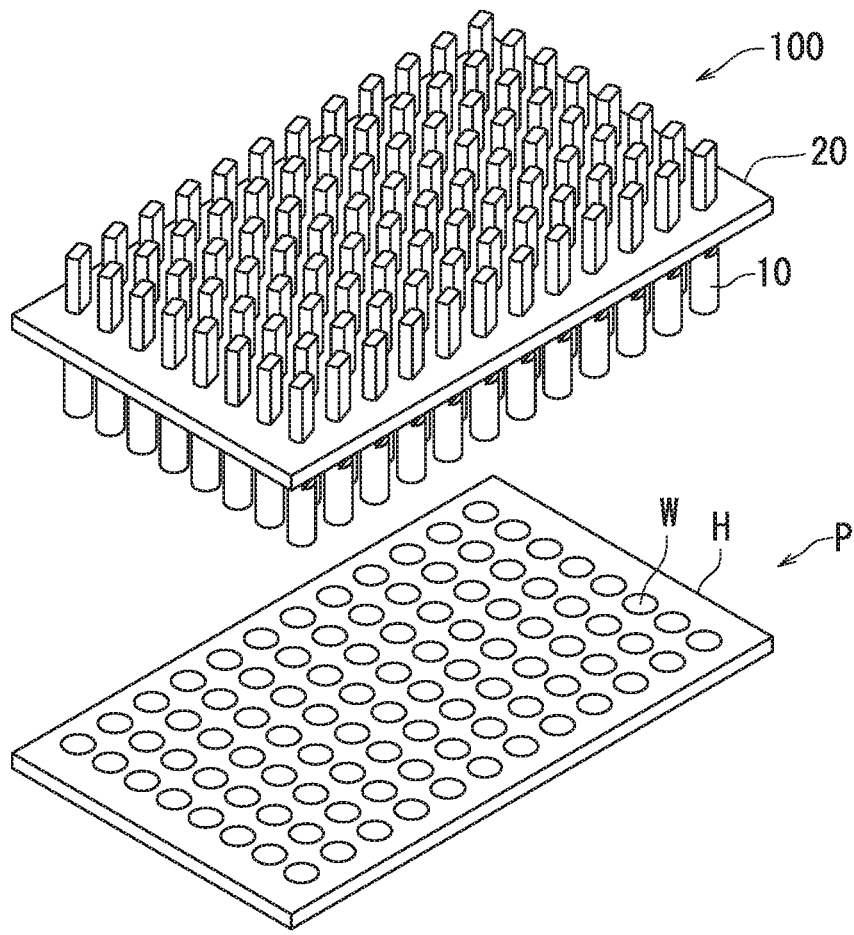
FIG. 5B is a schematic illustration depicting the ultrasound generation member, before being mounted on a microplate, according to the present embodiment.

FIG. 5B is a schematic illustration depicting the ultrasound generation member 100 before being mounted on a microplate P. The microplate P includes a flat section H. and wells W recessed in the flat section H. The wells W are separated from each other.

Here, respective centers of the holes of the holding member 20 into which the ultrasound generation elements 10 are individually inserted are individually positioned at respective places corresponding to centers of the wells W of the microplate P. A microplate that is shaped like the microplate P and has through holes in place of the wells may be employed as the holding member 20.

The holding member 20 holds the ultrasound generation elements 10, thereby allowing the ultrasound generation elements 10 to be mounted together on the microplate P with the positional relationship of the ultrasound generation elements 10 maintained.

Note that although the ultrasound generation elements 10 of the ultrasound generation member 100 are individually inserted into the wells W of the microplate P with the ultrasound generation elements 10 being in contact with target objects S in the above description, the present invention is not limited to this. The ultrasound generation elements 10 may be out of contact with the target objects S.

Figure 6:
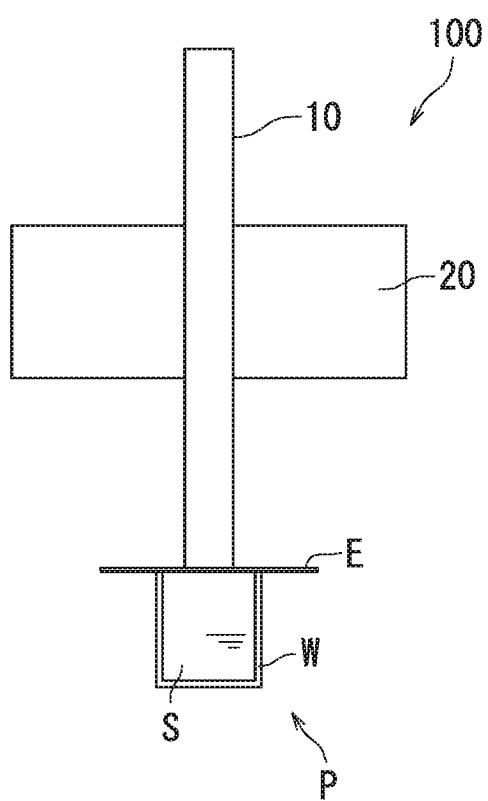
FIG. 6 is a schematic illustration depicting an ultrasound generation member according to an embodiment of the present invention.

An ultrasound generation member 100 according to an embodiment of the present invention will next be described with reference to FIG. 6. FIG. 6 is a schematic illustration depicting the ultrasound generation member 100 mounted on a microplate P.

As stated above with reference to FIG. 5, the ultrasound generation member 100 includes ultrasound generation elements 10 and a holding member 20. The ultrasound generation member 100 is mounted on the microplate P provided with wells W. Note that FIG. 6 illustrates one of the ultrasound generation elements 10, and one of the wells W in order to avoid overcomplicating the figure.

Target objects S are individually contained in the wells W of the microplate P, and a ceiling membrane E is stuck on an upper surface of the wells W. Thus, the wells W of the microplate P which individually contain the target objects S are sealed with the ceiling membrane E. For example, the ceiling membrane E is made of polyester. The ceiling membrane E is for example greater than or equal to 10 μm and less than or equal to 200 μm in thickness.

Here, the ceiling membrane E seals the wells W so that air and the like other than the target objects S does not enter the wells W. The ceiling membrane E is in contact with the target objects S. Therefore, when the ultrasound generation elements 10 are provided with voltage and generate vibration, the vibration is transmitted to the target objects S through the ceiling membrane E. Ultrasound generated by each ultrasound generation element 10 is consequently transmitted to a corresponding target object S.

The ultrasound generation member 100 according to the present embodiment prevents each ultrasound generation element 10 from being in direct contact with a corresponding target object S because the ceiling membrane E is interposed between the ultrasound generation elements 10 and the target objects S. The embodiment therefore makes it possible to, even if the target objects S are contaminants, avoid cleaning and/or discarding the ultrasound generation elements 10, and immediately use the ultrasound generation elements 10 in another application.

Unlike the ultrasonic generator of Patent Literature 1, the ultrasound generation member 100 according to the present embodiment enables the ultrasound generation elements 10 to individually emit ultrasound to the target objects S with high reproducibility because each ultrasound generation element 10 emits ultrasound through not a liquid but the ceiling membrane E.

Note that although the ultrasound generation elements 10 are mounted on the microplate P so that the ultrasound generation elements 10 individually correspond to the wells W in the above description with reference to FIGS. 1A to 6, the present invention is not limited to this. The ultrasound generation elements 10 may be disposed under the microplate P and individually emit ultrasound from respective bottom walls of the wells W. Alternatively, the ultrasound generation elements 10 may be arranged on respective sides of the wells W of the microplate P and individually emit ultrasound from respective side walls of the wells W.

In the ultrasound generation member 100 illustrated in FIG. 6, the ceiling membrane E is stuck to the microplate P so that the target objects S are individually sealed in the wells W, and the ultrasound generation elements 10 are disposed on the ceiling membrane E. The present invention is however not limited to this. The ultrasound generation elements 10 may individually emit ultrasound from the ceiling membrane E and/or the side walls to the wells W with the microplate P to which the ceiling membrane E is stuck turned upside down. In this case, air may be mixed into the wells W.

Each tip of the ultrasound generation elements 10 illustrated in FIGS. 2A, 2B, and 6 is flat, but is not limited to flat. Each tip of the ultrasound generation elements 10 may be shaped like a curved surface.

An ultrasound generation member 100 according to an embodiment of the present invention will next be described with reference to FIGS. 7A and 7B. Note that FIGS. 7A and 7B illustrate one of ultrasound generation elements 10, and one of wells W without depicting electrodes of the one ultrasound generation element 10 in order to avoid overcomplicating the figures.

Figure 7A:
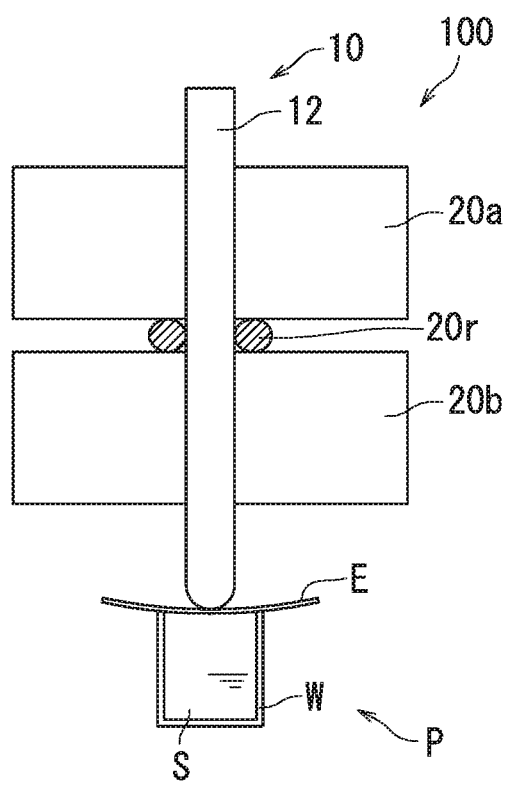
FIG. 7A is a schematic illustration depicting an ultrasound generation member according to an embodiment of the present invention.
Figure 7B:
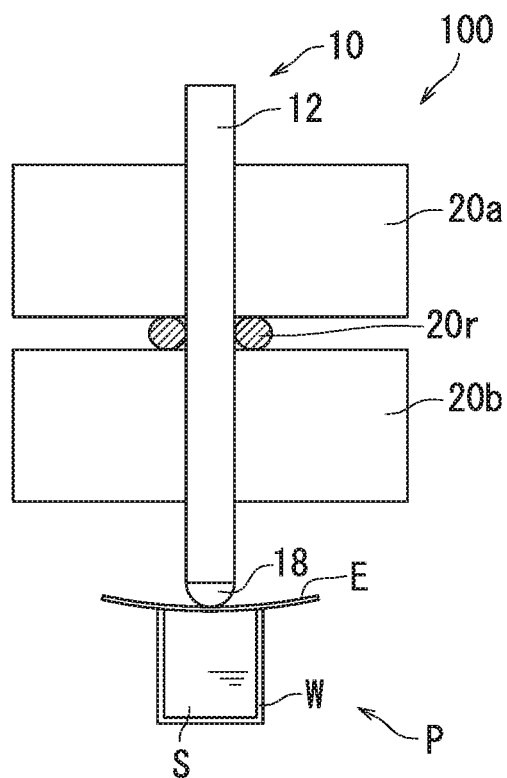
FIG. 7B is a schematic illustration depicting an ultrasound generation member according to an embodiment of the present invention.

FIG. 7A is a schematic illustration depicting the ultrasound generation member 100 according to the present embodiment. The ultrasound generation member 100 includes the ultrasound generation elements 10 and a holding member 20. The ultrasound generation member 100 is mounted on a microplate P provided with the wells W.

Here, each tip of the ultrasound generation elements 10 is shaped like a curved surface. For example, a tip of an oscillator 12 of each ultrasound generation element 10 is shaped into a curved surface.

In the ultrasound generation member 100 according to the present embodiment, the tip of each ultrasound generation element 10 has a salient surface. This enables each ultrasound generation element 10 to, even if a ceiling membrane E is slightly bent microscopically, be in reliable contact with a ceiling membrane E and transmit ultrasound to a corresponding target object S through the ceiling membrane E.

Here, the holding member 20 includes an upper holding layer 20a, a lower holding layer 20b, and sealing members 20r. The upper holding layer 20a has a plate shape, and is provided with holes individually corresponding to the ultrasound generation elements 10. Similarly, the lower holding layer 20b has a plate shape, and is provided with holes individually corresponding to the ultrasound generation elements 10.

Each sealing member 20r has, for example, an annular structure. The ultrasound generation elements 10 are individually inserted into respective holes of the sealing members 20r with each sealing member 20r surrounding an outer periphery of one corresponding ultrasound generation element 10. Each sealing member 20r is sandwiched between the upper holding layer 20a and the lower holding layer 20b. Each sealing member 20r is for example an O-ring. It is preferable that each sealing member 20r fix a node with less vibration of a corresponding oscillator 12 that vibrates during voltage application.

Note that although a tip of each oscillator 12 in the ultrasound generation member 100 according to the present embodiment illustrated in FIG. 7A is shaped like a curved surface in order to shape each tip of the ultrasound generation elements 10 into the curved surface, the present invention is not limited to this.

As illustrated in FIG. 7B, each ultrasound generation element 10 may further include a tip section 18 attached to a tip of a corresponding rod-shaped oscillator 12. The tip section 18 has for example a hemispherical shape and is attached to the tip of the oscillator 12 with adhesive or the like.

Note that although each ultrasound generation element 10 transmits ultrasound to a corresponding target object S through the ceiling membrane E that is several ten μm to several hundred μm in thickness in the above description with reference to FIGS. 6, 7A, and 7B, the present invention is not limited to this. Each ultrasound generation element 10 may transmit ultrasound to a corresponding target object S through a rod-shaped member.

Figure 8:
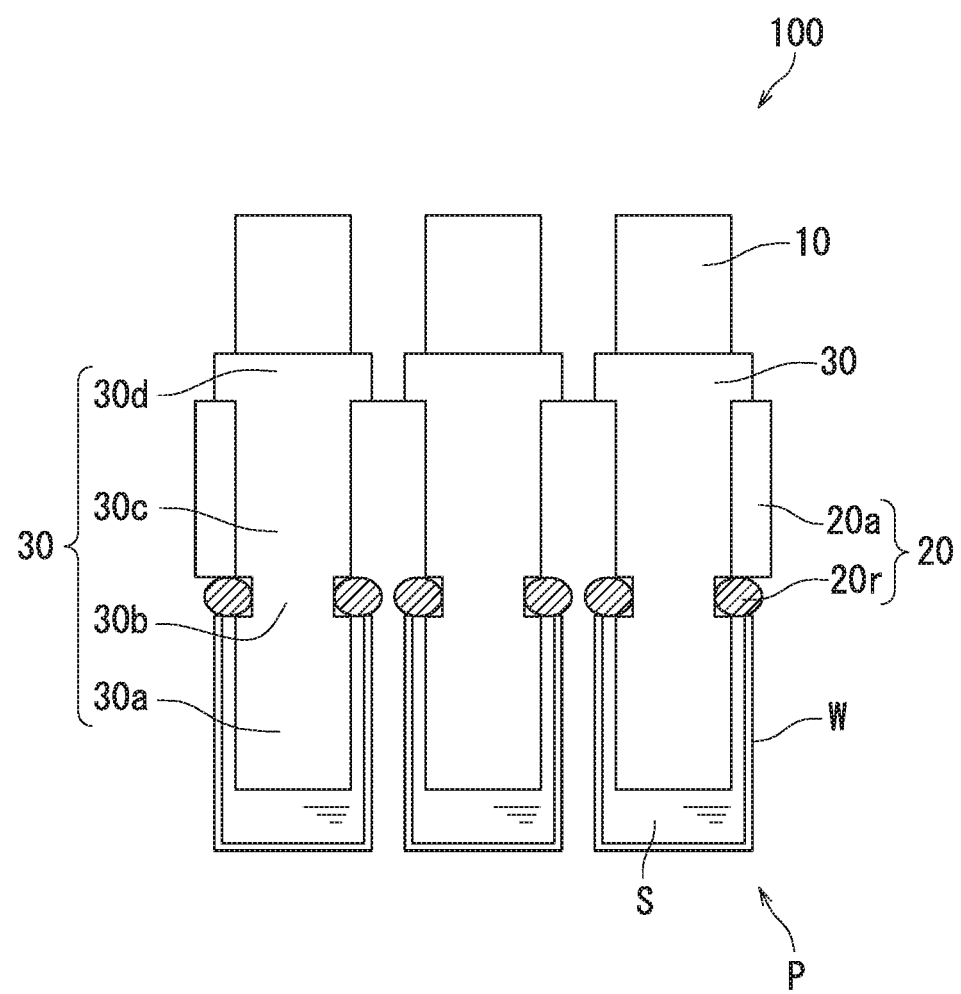
FIG. 8 is a schematic illustration depicting an ultrasound generation member according to an embodiment of the present invention.

An ultrasound generation member 100 according to an embodiment of the present invention will next be described with reference to FIG. 8. FIG. 8 is a schematic illustration depicting the ultrasound generation member 100 according to the present embodiment.

The ultrasound generation member 100 is mounted on a microplate P provided with wells W. The ultrasound generation member 100 includes ultrasound generation elements 10, a holding member 20, and acoustic coupling members 30. Of the ultrasound generation elements 10 and the wells W, three ultrasound generation elements 10 and three wells W are respectively illustrated in FIG. 8 in order to avoid overcomplicating the figure.

A tip of each ultrasound generation element 10 is connected to a corresponding acoustic coupling member 30. Typically, the tip of each ultrasound generation element 10 is connected to the corresponding acoustic coupling member 30 with adhesive.

The holding member 20 includes a holding layer 20a and sealing members 20r. The holding layer 20a has a plate shape, and is provided with holes individually corresponding to the acoustic coupling members 30. A microplate that is shaped like the microplate P and has through holes in place of the wells may be employed as the holding layer 20a.

Each sealing member 20r has an annular structure. The acoustic coupling members 30 are individually inserted into respective holes of the sealing members 20r with each sealing member 20r surrounding an outer periphery of one corresponding acoustic coupling member 30. Each sealing member 20r is for example an O-ring.

Note that unlike the ultrasound generation member 100 described above with reference to FIG. 7A, in the ultrasound generation member 100 according to the present embodiment, each sealing member 20r is sandwiched between the holding layer 20a and a side wall defining a corresponding well W of the microplate P around a corresponding acoustic coupling member 30.

Each acoustic coupling member 30 transmits vibration of a corresponding ultrasound generation element 10 to a target object S in a corresponding well W of the microplate P. Each acoustic coupling member 30 has a rod shape.

Each acoustic coupling member 30 is formed of a hard material suitable for transmitting ultrasound while suppressing attenuation thereof. For example, each acoustic coupling member 30 is made of quartz. Alternatively, each acoustic coupling member 30 may be made of sapphire, optical glass, or a thin film polymer such as polyimide.

Each acoustic coupling member 30 includes a well insertion section 30a, a seal joint section 30b, a penetration section 30c, and a vibration coupling section 30d. The well insertion section 30a is joined to the seal joint section 30b, while the seal joint section 30b is joined to the penetration section 30c. The penetration section 30c is also joined to the vibration coupling section 30d.

The well insertion section 30a is inserted into a corresponding well W of the microplate P and is in contact with a corresponding target object S. The seal joint section 30b is surrounded by a corresponding sealing member 20r. The seal joint section 30b has width that is narrower than both width of the well insertion section 30a and width of the penetration section 30c. The seal joint section 30b also has height that is almost the same as a cross section diameter of each sealing member 20r. Each sealing member 20r is positioned and surrounded by the well insertion section 30a, the seal joint section 30b, and the penetration section 30c of a corresponding acoustic coupling member 30.

The penetration section 30c is elongated so as to penetrate a hole of a corresponding holding layer 20a. The vibration coupling section 30d is in contact with an ultrasound generation element 10. The vibration coupling section 30d has width that is wider than width of the penetration section 30c.

In the ultrasound generation member 100 according to the present embodiment, each acoustic coupling member 30 is provided between a corresponding ultrasound generation element 10 and a corresponding target object S. Each ultrasound generation element 10 is accordingly not in direct contact with a corresponding target object S. It is therefore possible to, even if the target objects S are contaminants, avoid cleaning and/or discarding the ultrasound generation elements 10, and immediately use the ultrasound generation elements 10 in another application.

Each acoustic coupling member 30 efficiently transmits vibration of a corresponding ultrasound generation element 10 to a corresponding target object S. An ultrasound emission device 200 according to the present embodiment enables efficient emission of ultrasound to each target object S.

Note that the ultrasound emission device 200 according to the present embodiment may not only individually emit ultrasound to the target objects S, but also measure intensity of the ultrasound transmitted to each target object S.

Figure 9:
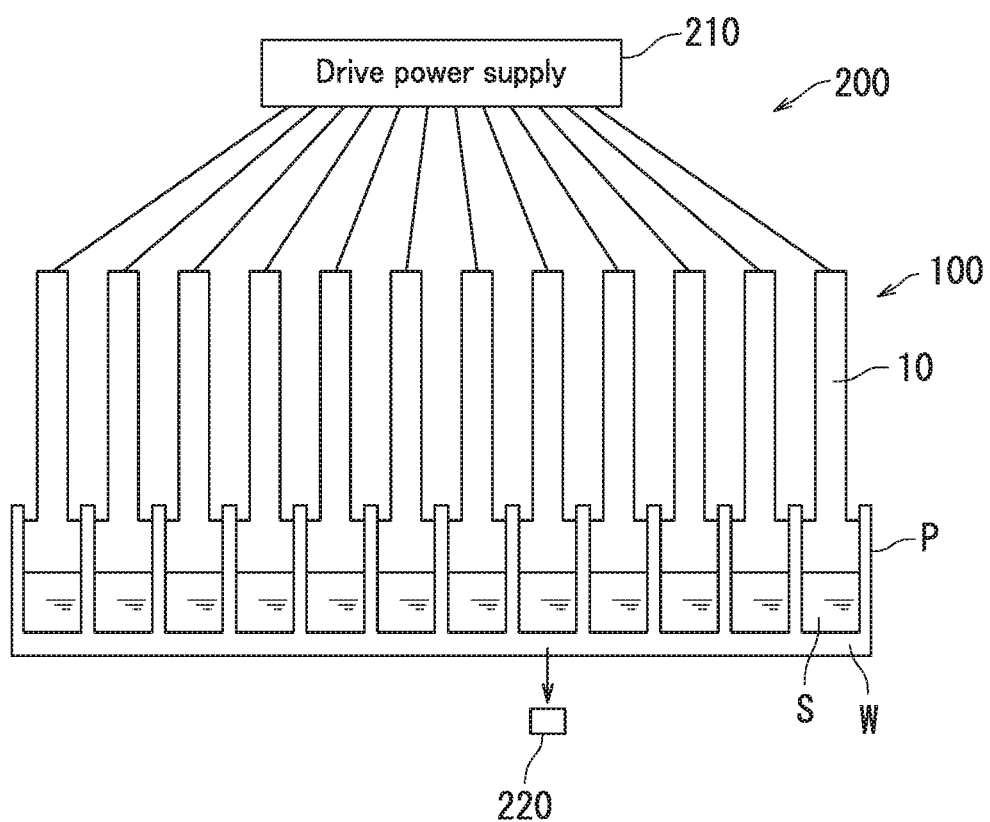
FIG. 9 is a schematic illustration depicting an ultrasound emission device according to an embodiment of the present invention.

An ultrasound emission device 200 according to an embodiment of the present invention will next be described with reference to FIG. 9. FIG. 9 is a schematic illustration of the ultrasound emission device 200 according to the present embodiment. The ultrasound emission device 200 illustrated in FIG. 9 has a configuration similar to that of the ultrasound emission device 200 described above with reference to FIG. 3 except that the present embodiment includes a sound pressure measuring device 220. Duplicate descriptions are therefore omitted in order to avoid redundancy.

The ultrasound emission device 200 includes an ultrasound generation member 100, a drive power supply 210, and the sound pressure measuring device 220. The sound pressure measuring device 220 measures sound pressure with respect to a target object S in each well W of a microplate P. For example, the sound pressure measuring device 220 is a microphone.

The ultrasound generation member 100 is mounted on the microplate P provided with the wells W. The sound pressure measuring device 220 is disposed at a position opposite the ultrasound generation member 100 through the microplate P. For example, the sound pressure measuring device 220 is disposed at a position opposite a specific well W of the microplate P.

When the drive power supply 210 applies voltage across ultrasound generation elements 10 of the ultrasound generation member 100, each of the ultrasound generation elements 10 emits ultrasound to the target object S in a corresponding well W. The sound pressure measuring device 220 measures sound pressure with respect to each target object S. For example, the sound pressure measuring device 220 is sequentially moved so as to be opposite every well W of the microplate P, thereby enabling measurement of sound pressure with respect to every target object S. In the ultrasound emission device 200 according to the present embodiment, it can be confirmed that the ultrasound generation member 100 appropriately emits ultrasound to each well W of the microplate P, and/or each ultrasound generation element 10 correctly operates.

Note that the ultrasound emission device 200 may not only measure sound pressure, but also adjust intensity of ultrasound to be transmitted to each target object S based on a corresponding measurement result.

Figure 10:
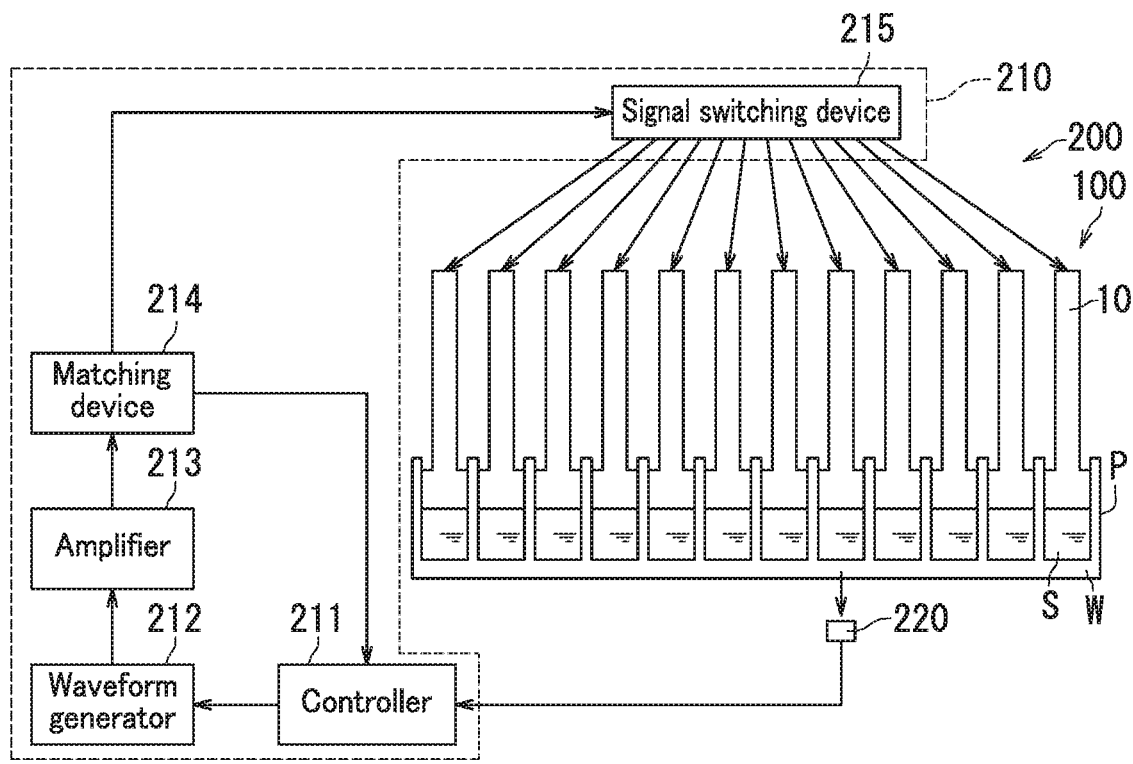
FIG. 10 is a schematic illustration depicting an ultrasound emission device according to an embodiment of the present invention.

An ultrasound emission device 200 according to an embodiment of the present invention will next be described with reference to FIG. 10. FIG. 10 is a schematic illustration of the ultrasound emission device 200 according to the present embodiment. The ultrasound emission device 200 includes an ultrasound generation member 100, a drive power supply 210, and a sound pressure measuring device 220.

The ultrasound emission device 200 illustrated in FIG. 10 has a configuration similar to that of the ultrasound emission device 200 described above with reference to FIG. 4A except that the present embodiment includes the sound pressure measuring device 220, and a signal through a matching device 214 enters a controller 211. Duplicate descriptions are therefore omitted in order to avoid redundancy.

The sound pressure measuring device 220 measures sound pressure with respect to a target object S in a specific well W of a microplate P. The sound pressure measuring device 220 provides a measurement result to the controller 211.

In addition, as stated above, a signal that is output from an amplifier 213 is output toward the ultrasound generation elements 10 after impedance matching in the matching device 214. In the ultrasound emission device 200 according to the present embodiment, the controller 211 is also provided with the signal that is output toward the ultrasound generation elements 10 through the matching device 214.

The controller 211 adjusts amplitude of a waveform to be designated to a waveform generator 212 based on the signal that is output toward an ultrasound generation element 10 in the specific well W of the microplate P, and intensity of ultrasound generated from the ultrasound generation element 10. For example, when intensity of the ultrasound emitted from the ultrasound generation element 10 is relatively smaller than an input signal of the ultrasound generation element 10, the controller 211 increases amplitude of a waveform to be designated to the waveform generator 212. Alternatively, when intensity of the ultrasound emitted from the ultrasound generation element 10 is relatively larger than the input signal of the ultrasound generation element 10, the controller 211 decreases the amplitude of the waveform to be designated to the waveform generator 212.

The ultrasound emission device 200 according to the present embodiment performs feedback control based on intensity of ultrasound generated from a specific ultrasound generation element 10, thereby enabling emission of ultrasound of more accurate intensity to a target object S in each well W of the microplate P.

Note that when ultrasound is transmitted to each target object S, properties thereof may change. For example, by transmitting ultrasound to a target object S, size thereof may change, or the target object S may be induced to an induced object. The ultrasound emission device 200 may therefore be employed as a part of an ultrasound denaturation observation device for observing a denaturation of each target object S due to ultrasound emission.

Figure 11:
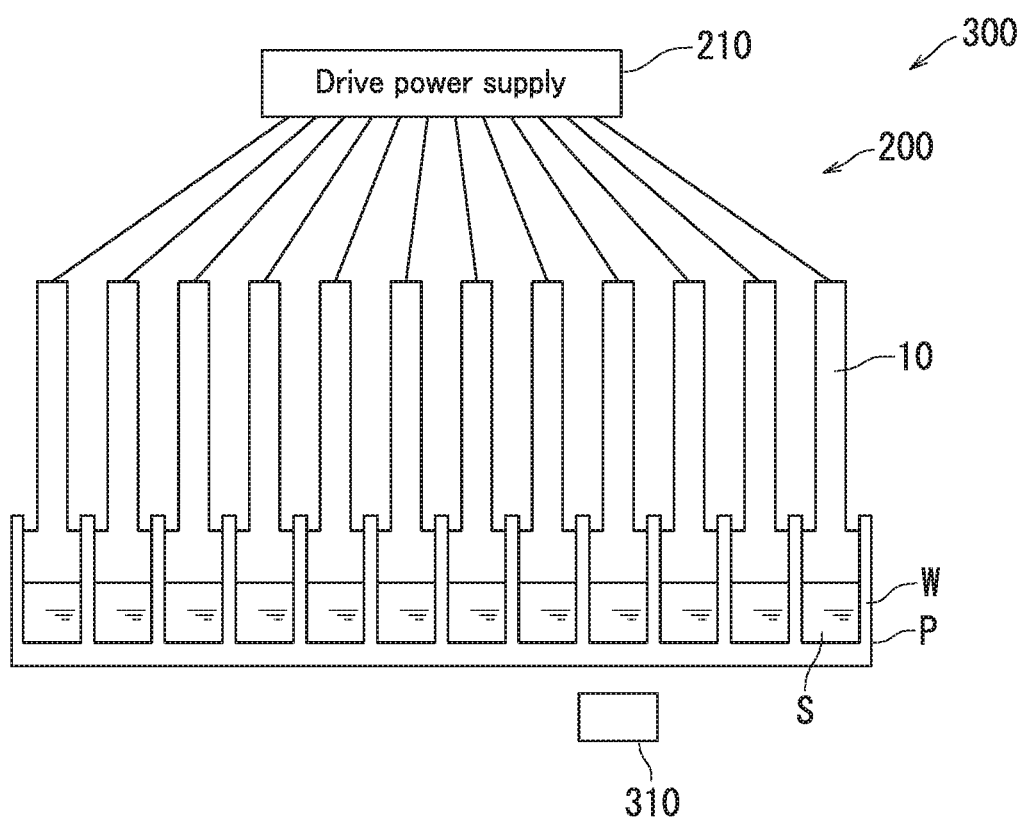
FIG. 11 is a schematic illustration depicting an ultrasound denaturation observation device according to an embodiment of the present invention.

An ultrasound denaturation observation device 300 according to an embodiment of the present invention will next be described with reference to FIG. 11. FIG. 11 is a schematic illustration of the ultrasound denaturation observation device 300 according to the present embodiment.

The ultrasound denaturation observation device 300 includes an ultrasound emission device 200 and an observation section 310. The ultrasound emission device 200 includes an ultrasound generation member 100 and a drive power supply 210. The ultrasound generation member 100 is mounted on a microplate P provided with wells W. The wells W individually contain the target objects S. The observation section 310 observes a denaturation due to ultrasound emission of the target object S in each well W.

When the drive power supply 210 applies voltage to the ultrasound generation member 100, the ultrasound generation member 100 individually emits ultrasound to the target objects S in the wells W of the microplate P. The observation section 310 observes the denaturation due to ultrasound emission of the target object S in each well W.

The observation section 310 may monitor the target object S itself in each well W. Alternatively, the observation section 310 may monitor an induced object induced from the target object S due to the ultrasound emission.

The observation section 310 may capture image data of the target object S in each well W. For example, the observation section 310 includes an image sensor. The observation section 310 may include a charge coupled device (CCD) camera.

Note that by emitting ultrasound to each target object S, an absorption property and a fluorescence property thereof may change. When a target object S changes to an induced object due to the ultrasound emission and the induced object exhibits a singular response to light of a specific wavelength, absorption and fluorescence do not occur even when the target object S is struck by the light of the specific wavelength, whereas absorption and fluorescence occur in the induced object induced from the target object S when the induced object is struck by the light of the specific wavelength. In this case, an amount of the produced induced object can be measured by emitting light to be absorbed by the induced object to measuring intensity of fluorescence from the induced object.

Figure 12:
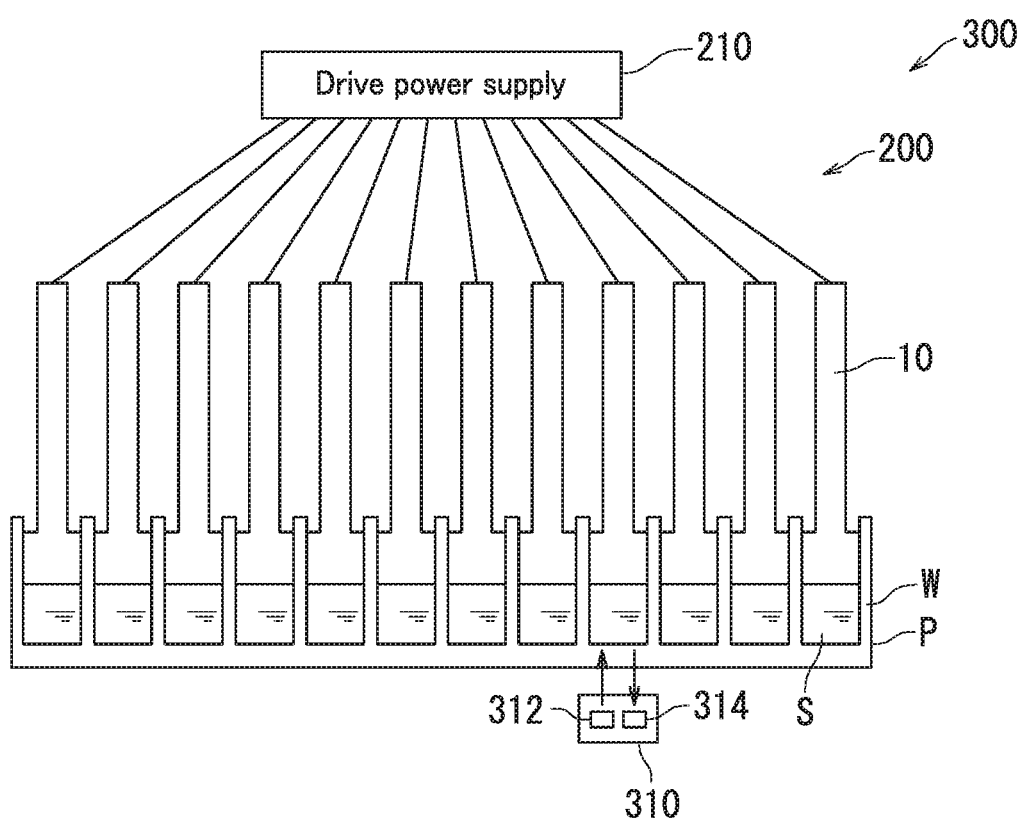
FIG. 12 is a schematic illustration depicting an ultrasound denaturation observation device according to an embodiment of the present invention.

An ultrasound denaturation observation device 300 according to an embodiment of the present invention will next be described with reference to FIG. 12. FIG. 12 is a schematic illustration of the ultrasound denaturation observation device 300 according to the present embodiment.

The ultrasound denaturation observation device 300 illustrated in FIG. 12 has a configuration similar to that of the ultrasound denaturation observation device 300 described above with reference to FIG. 11 except that an observation section 310 in the present embodiment includes a light emitting section 312 and a light detecting section 314. Duplicate descriptions are therefore omitted in order to avoid redundancy.

As stated above, the observation section 310 includes the light emitting section 312 and the light detecting section 314. The light emitting section 312 focuses light into a specific well W of a microplate P. The light detecting section 314 detects a specific light from the specific well W of the microplate P.

The ultrasound denaturation observation device 300 according to the present embodiment emits ultrasound, thereby enabling observation of newly produced induced object that absorbs the specific light and emits a specific light.

Note that although the ultrasound generation member 100 includes the ultrasound generation elements 10 in the above description with reference to FIGS. 1A to 12, the present invention is not limited to this. The ultrasound generation member 100 may include only one ultrasound generation element 10.

Figure 13:
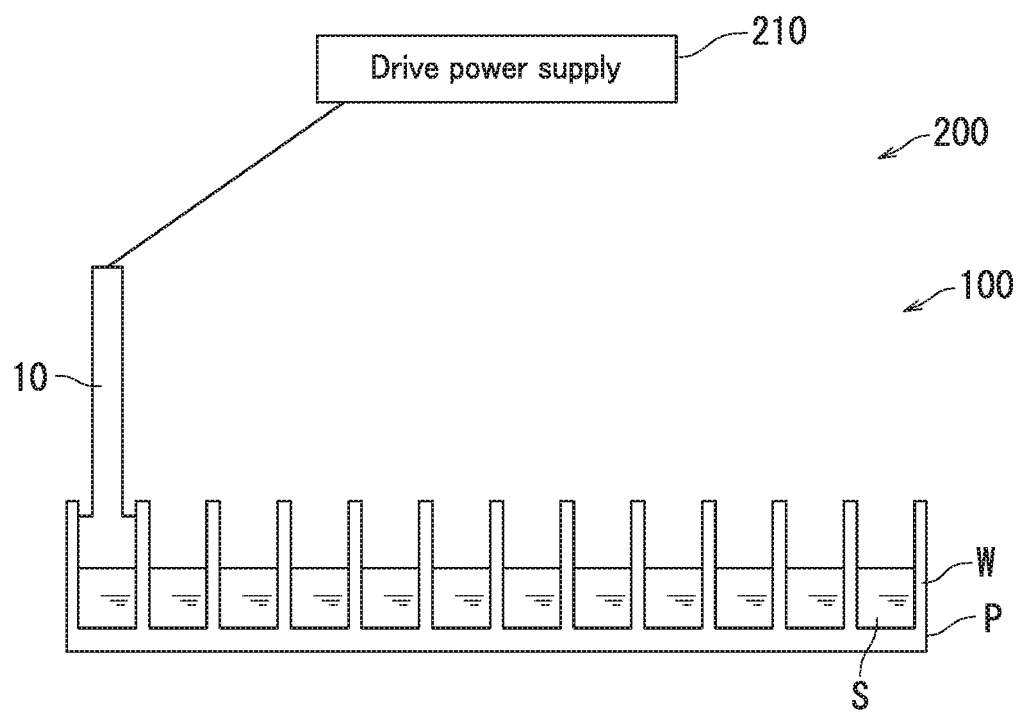
FIG. 13 is a schematic illustration depicting an ultrasound emission device according to an embodiment of the present invention.

An ultrasound emission device 200 according to an embodiment of the present invention will next be described with reference to FIG. 13. FIG. 13 is a schematic illustration depicting the ultrasound emission device 200.

The ultrasound emission device 200 includes an ultrasound generation member 100 and a drive power supply 210. The ultrasound generation member 100 includes one ultrasound generation element 10. A microplate P is provided with wells W, and the wells W individually contain target objects S. The ultrasound generation element 10 emits ultrasound to the target object S contained in each of the wells W.

For example, after the ultrasound generation element 10 emits ultrasound from a predetermined emitting position to the target object S in one well W of the wells, a user may move the ultrasound generation element 10 to an emitting position with respect to the target object S in a different well W. The ultrasound generation element 10 subsequently emits ultrasound to the target object S in the different well W.

Note that although the user moves the ultrasound generation element 10 to the emitting position with respect to the different well W in the above description with reference to FIG. 13, the present invention is not limited to this. The ultrasound generation element 10 may be appropriately controlled and moved to an emitting position with respect to the target object S in a different well W.

Figure 14:
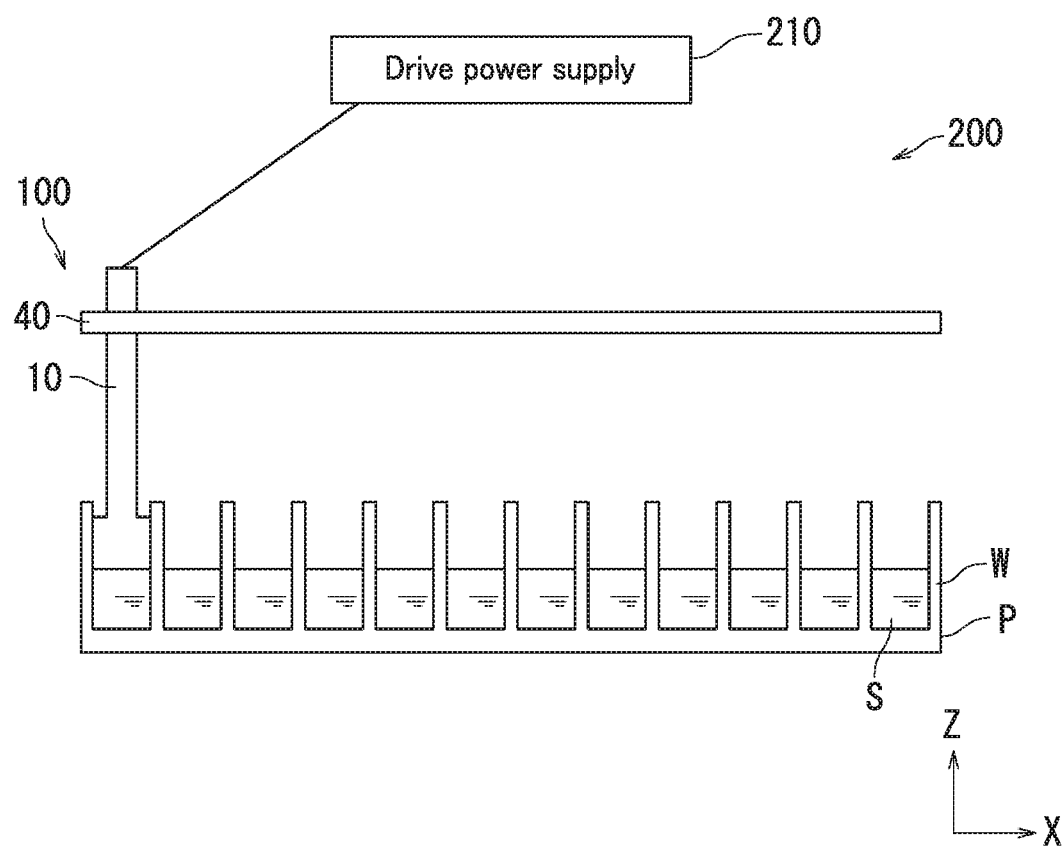
FIG. 14 is a schematic illustration depicting an ultrasound emission device according to an embodiment of the present invention.

An ultrasound emission device 200 according to an embodiment of the present invention will next be described with reference to FIG. 14. FIG. 14 is a schematic illustration depicting the ultrasound emission device 200.

The ultrasound emission device 200 includes an ultrasound generation member 100 and a drive power supply 210. The ultrasound generation member 100 includes one ultrasound generation element 10 and a moving section 40. The moving section 40 moves the ultrasound generation element 10.

A microplate P is provided with wells W, and the wells W individually contain target objects S. The ultrasound generation element 10 sequentially emits ultrasound to the target object S included in each of the wells W.

The moving section 40 moves the ultrasound generation element 10 to an emitting position with respect to the target object S in each of the wells W. The ultrasound generation element 10 is movable in an X-direction by the moving section 40. Similarly, the ultrasound generation element 10 is movable in a Y-direction (not illustrated in FIG. 14) orthogonal to both the X-direction and a Z-direction. The ultrasound generation element 10 is further movable in the Z-direction by the moving section 40.

For example, after the ultrasound generation element 10 emits ultrasound from a predetermined emitting position to the target object S in one well W of the wells W, the moving section 40 moves the ultrasound generation element 10 up in the Z-direction. The moving section 40 then moves the ultrasound generation element 10 in a direction parallel to the X-direction and/or the Y-direction, and subsequently moves the ultrasound generation element 10 down in the Z-direction. Thus, the ultrasound generation element 10 is moved to an emitting position with respect to the target object S in a different well W of the wells W, and subsequently the ultrasound generation element 10 emits ultrasound to the target object S in the different well W.

Note that although the ultrasound generation element 10 sequentially emits ultrasound to the target object S in each of the wells W provided for the microplate P in the above description with reference to FIGS. 13 and 14, the present invention is not limited to this. The ultrasound generation element 10 may emit ultrasound to the target object S in a single container.

Although the one ultrasound generation element 10 sequentially emits ultrasound to the target object S in each of the wells W in the above description with reference to FIGS. 13 and 14, the present invention is not limited to this. The ultrasound generation member 100 is provided with two or more ultrasound generation elements 10, each of which sequentially emits ultrasound to each target object S in wells W.

Figure 15:
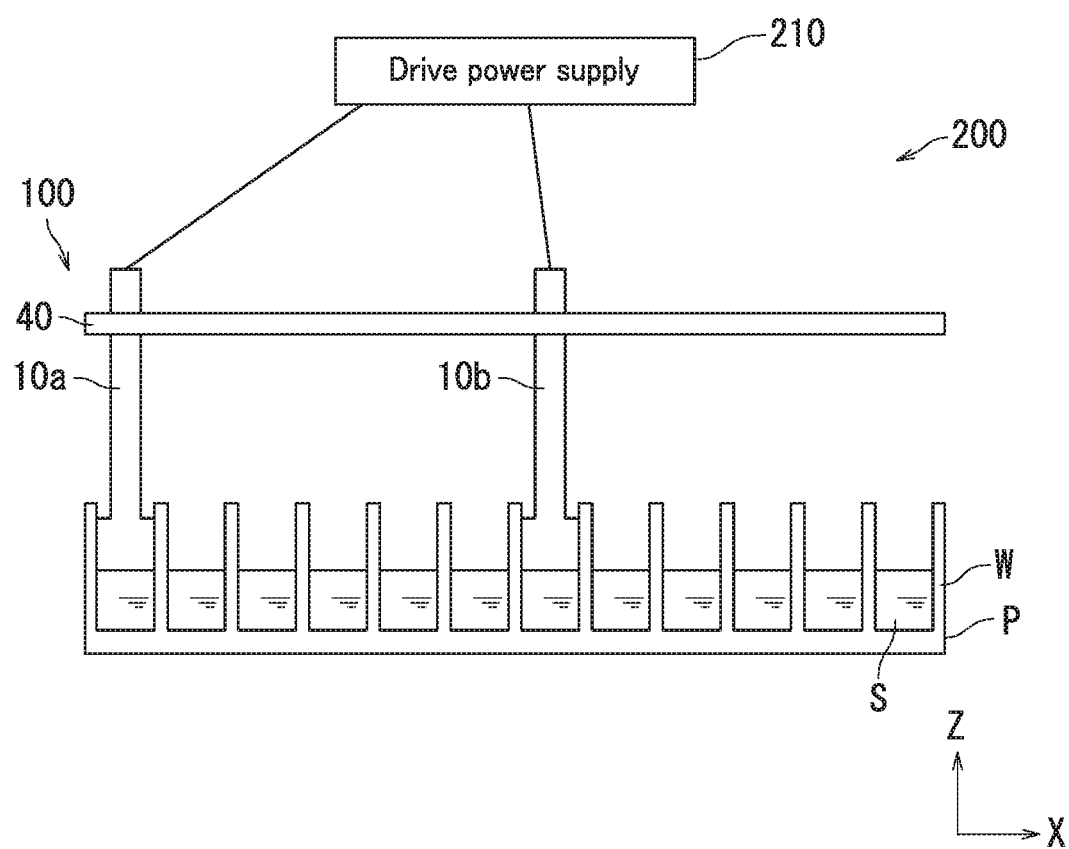
FIG. 15 is a schematic illustration depicting an ultrasound emission device according to an embodiment of the present invention.

An ultrasound emission device 200 according to an embodiment of the present invention will hereinafter be described with reference to FIG. 15. FIG. 15 is a schematic illustration depicting the ultrasound emission device 200.

The ultrasound emission device 200 includes an ultrasound generation member 100 and a drive power supply 210. The ultrasound generation member 100 includes a first ultrasound generation element 10a, a second ultrasound generation element 10b, and a moving section 40. The moving section 40 moves the first and second ultrasound generation elements 10a and 10b.

The first ultrasound generation element 10a emits ultrasound to the target object S in each of wells W in a left half of the wells W. On the other hand, the second ultrasound generation element 10b emits ultrasound to the target object S in each of wells W in a right half of the wells W.

The moving section 40 moves the first and second ultrasound generation elements 10a and 10b to emitting positions with respect to respective corresponding target objects S in the wells W. The first and second ultrasound generation elements 10a and 10b are movable in an X-direction, a Y-direction, and/or a Z-direction by the moving section 40.

For example, the first ultrasound generation element 10a emits ultrasound from a predetermined emitting position to the target object S in a well W in a first row, while the second ultrasound generation element 10b emits ultrasound from a predetermined emitting position to the target object S in a well W in a seventh row. The moving section 40 subsequently lifts the first and second ultrasound generation elements 10a and 10b up in the Z-direction.

The moving section 40 then moves the first ultrasound generation element 10a above the well W in a second row in the X-direction in a parallel manner, and moves the second ultrasound generation element 10b above the well W in an eighth row in the X-direction in a parallel manner. The moving section 40 subsequently moves the first and second ultrasound generation elements 10a and 10b down in the Z-direction.

The first ultrasound generation element 10a then emits ultrasound from a predetermined emitting position to the target object S in a well W in the second row, while the second ultrasound generation element 10b emits ultrasound from a predetermined emitting position to the target object S in a well W in the eighth row. Thus, the first and second ultrasound generation elements 10a and 10b moves to respective emitting positions with respect to respective target objects S in the wells W in respective different rows and/or the wells W in respective different columns, and then individually emit ultrasound to the target objects S in the wells W.

A measurement result of the present embodiment will next be described in comparison with a reference example.

An ultrasound emission device including an ultrasound generation member 100 having a configuration as illustrated in FIGS. 5A and 5B was prepared as an embodiment.

A β2-microglobulin solution (containing 100 mM NaCl, and 5 μM thioflavin T, pH 2.5) was added in each of 16 wells W of a microplate P, and the microplate P was set at a temperature of 37° C. The thioflavin T functions as amyloid specific fluorochrome.

The ultrasound generation member 100 including 12 ultrasound generation elements 10 was then mounted on the microplate P. Each ultrasound generation element 10 was 55 mm in height T, and was 20 mm$^2$ in sectional area. The ultrasound generation elements 10 were individually provided for 12 wells W of 16 wells W individually containing amyloid β. In this state, ultrasound emission and interruption thereof were repeated. The 12 ultrasound generation elements 10 were set to have similar ultrasound intensity and emission time. After completion of the repetition of the ultrasound emission and interruption thereof, fluorescence with a wavelength of about 490 nm was detected by focusing light with a wavelength of about 450 nm as excitation light on each sample in the microplate P.

In addition, an ultrasound emission device including an ultrasonic generator having the configuration of Patent Literature 1 was prepared as the ultrasound emission device of the reference example.

A β2-microglobulin solution (containing 100 mM NaCl, and 5 μM thioflavin T, pH 2.5) was added in each of 96 wells W of a microplate P, and the microplate P was set at a temperature of 37° C. The ultrasound emission device was then mounted on the microplate P. In this state, ultrasound emission and interruption thereof were repeated. After completion of the repetition of the ultrasound emission and interruption thereof, fluorescence with a wavelength of about 490 nm was detected by focusing light with a wavelength of about 450 nm as excitation light on each sample in the microplate P.

Figure 16A:
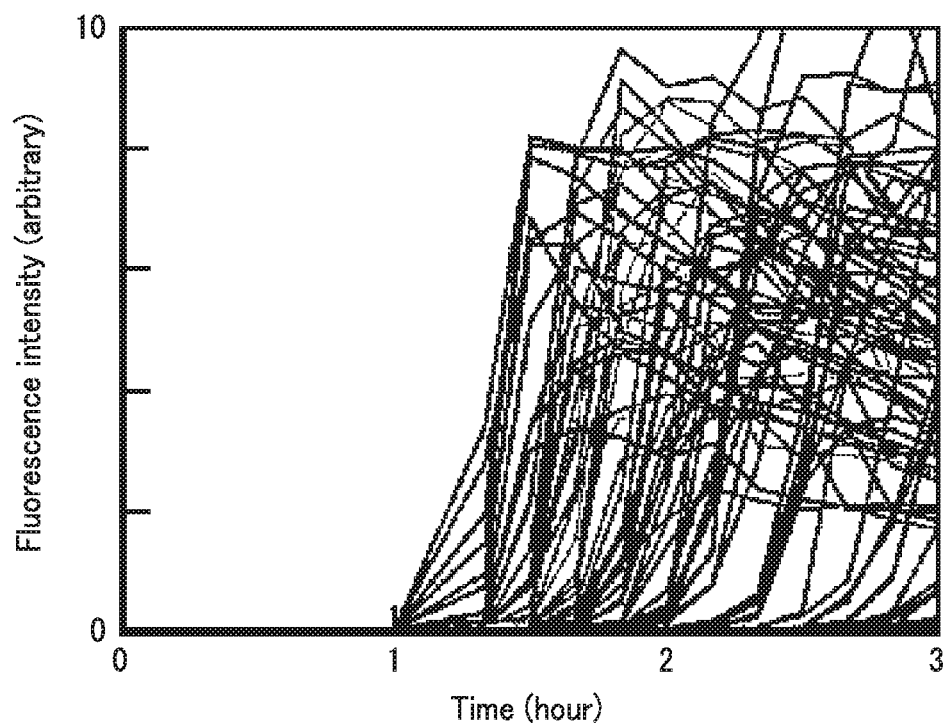
FIG. 16A is a graph depicting an intensity change with time of fluorescence emitted from amyloid fibrils in the case of an ultrasound emission device as a reference example.
Figure 16B:
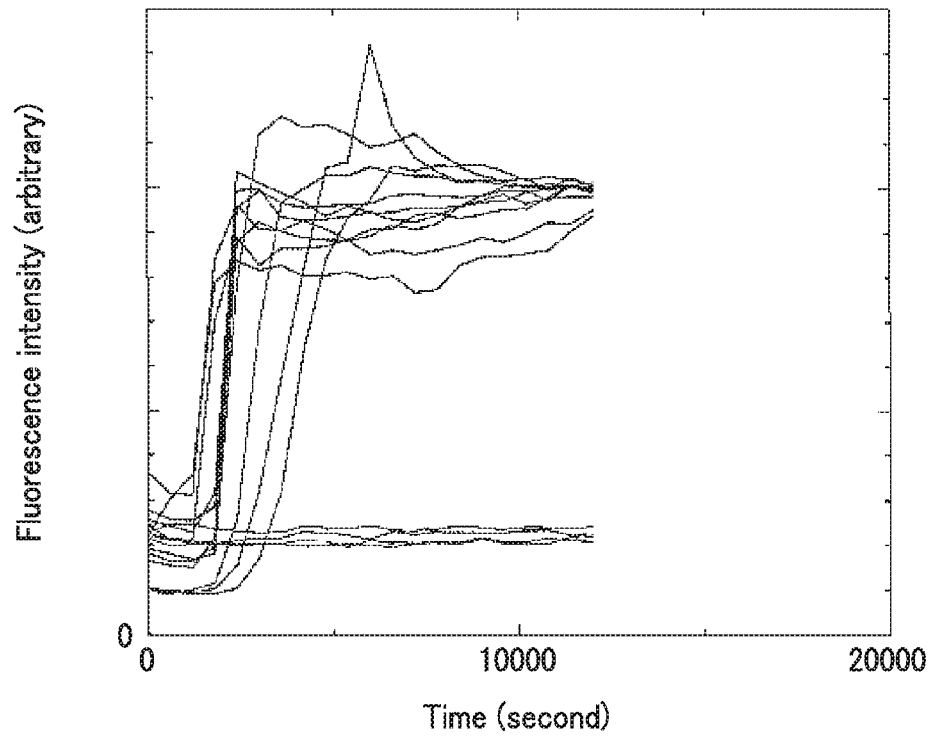
FIG. 16B is a graph depicting an intensity change with time of fluorescence emitted from amyloid fibrils in the case of an ultrasound emission device according to an embodiment.

FIG. 16A is a graph depicting an intensity change with time of fluorescence emitted from amyloid fibrils in the case of the ultrasound emission device as the reference example. FIG. 16B is a graph depicting an intensity change with time of fluorescence emitted from amyloid fibrils in the case of the ultrasound emission device according to the present embodiment.

In the ultrasound emission device as the reference example, identical ultrasound generation elements emitted ultrasound to the 96 wells. However, as can be seen from FIG. 16A, a change in fluorescence intensity greatly varied according to positions of the wells W of the microplate P.

FIG. 16B depicts a similar result for amyloid β. In the ultrasound emission device according to the present embodiment, the fluorescence intensity of each sample in the 12 wells W to which the ultrasound is transmitted began to increase at almost the same timing, and a change in fluorescence intensity for each well W hardly varied. Fluorescence from 4 wells W to which no ultrasound was transmitted was not observed.

As stated above, the present embodiment enables emission of ultrasound controlled for each of the target objects in the specific containers.

Note that although the wells W (individual containers) are arranged in the microplate P in a matrix with rows and columns, the present invention is not limited to this. The individual containers need not necessarily be arranged in a matrix, but may be aligned in a straight line. Alternatively, the individual containers may be arranged in any manner.

Although the wells W (individual containers) individually containing the target objects to receive ultrasound from the ultrasound generation elements 10 of the ultrasound generation member 100 are integrally configured on the one microplate P in the above description, the present invention is not limited to this. The individual containers need not necessarily be integrally configured. For examples, the individual containers may be discrete containers that are individually movable and arranged separately from each other, and the ultrasound generation elements 10 of the ultrasound generation member 100 may individually emit ultrasound to the target objects in the discrete containers.

INDUSTRIAL APPLICABILITY

The ultrasound generation members according to the embodiments can be applied to various applications using ultrasound.

REFERENCE SIGNS LIST

10 Ultrasound generation element
20 Holding member
100 Ultrasound generation member

The invention claimed is:

1. An ultrasound generation member, comprising
a plurality of ultrasound generation elements each configured to emit ultrasound to a target object in a corresponding one container of a plurality of containers, wherein
the ultrasound generation elements each include:
an oscillator formed of a piezoelectric material and elongated in a longitudinal direction thereof;
a first electrode provided for the oscillator, the first electrode having a first surface exposed to outside and a second surface covering a portion of the oscillator; and
a second electrode provided for the oscillator, the second electrode having a first surface exposed to outside and a second surface covering another portion of the oscillator.

2. The ultrasound generation member according to claim 1, wherein
in each of the ultrasound generation elements, the first electrode and the second electrode are elongated in a direction that is the same as the longitudinal direction in which the oscillator is elongated.

3. The ultrasound generation member according to claim 1, wherein
the ultrasound generation elements each further includes an acoustic coupling member connected to the oscillator.

4. The ultrasound generation member according to claim 1, further comprising
a holding member that holds the plurality of ultrasound generation elements.

5. The ultrasound generation member according to claim 4, wherein
the holding member is provided with holes each corresponding to one of the ultrasound generation elements.

6. An ultrasound emission device, comprising
the ultrasound generation member according to claim 1, and
a drive power supply configured to apply voltage across the plurality of ultrasound generation elements of the ultrasound generation member.

7. The ultrasound emission device according to claim 6, wherein
the drive power supply applies the voltage across the plurality of ultrasound generation elements so that each of the plurality of ultrasound generation elements sequentially emits ultrasound.

8. An ultrasound denaturation observation device, comprising
the ultrasound emission device according to claim 6, and
an observation section configured to observe a denaturation of the target object in the corresponding one container.

9. The ultrasound generation member according to claim 1, wherein
in each of the ultrasound generation elements,
the oscillator has
a first portion to be inserted to the target object in the corresponding one container, and
a second portion connected to the first potion,
the first electrode is provided for the second portion of the oscillator, and
the second electrode is provided for the second portion of the oscillator and located opposite to the first electrode.

10. The ultrasound generation member according to claim 1, wherein
the ultrasound generation elements are greater than or equal to 30 mm and less than or equal to 100 mm in height, and greater than or equal to 3 mm and less than or equal to 6 mm in width.

11. The ultrasound generation member according to claim 1, wherein
the ultrasound generation elements are greater than or equal to 50 mm and less than or equal to 60 mm in height, and greater than or equal to 4 mm and less than or equal to 5 mm in width.

* * * * *